United States Patent [19]

Mitchen

[11] Patent Number: 5,014,718

[45] Date of Patent: May 14, 1991

[54] BLOOD COLLECTION AND TESTING METHOD

[75] Inventor: Joel R. Mitchen, Mundelein, Ill.

[73] Assignee: Safety Diagnostics, Inc., Evanston, Ill.

[21] Appl. No.: 411,083

[22] Filed: Sep. 22, 1989

Related U.S. Application Data

[63] Continuation-in-part of Ser. No. 147,138, Jan. 22, 1988, abandoned.

[51] Int. Cl.⁵ .............................................. A61B 17/32
[52] U.S. Cl. ..................................... 128/771; 606/181
[58] Field of Search ....................... 128/760, 763–765, 128/770, 771; 606/181, 182

[56] References Cited

U.S. PATENT DOCUMENTS

| | | | |
|---|---|---|---|
| 3,068,855 | 12/1962 | Furlong, Jr. | 128/2 |
| 3,672,368 | 6/1972 | Schwartz | 128/218 N |
| 3,828,775 | 8/1974 | Armel | 128/218 N |
| 4,151,832 | 5/1979 | Hamer | 128/765 |
| 4,436,098 | 3/1984 | Kaufman | 128/766 |
| 4,637,403 | 1/1987 | Garcia et al. | 128/770 |
| 4,643,200 | 2/1987 | Jennings, Jr. | 128/763 |
| 4,660,570 | 4/1987 | Dombrowski | 128/765 |
| 4,675,159 | 6/1987 | Sioufi | 128/764 |
| 4,844,098 | 7/1989 | Mitchen | 128/765 |

FOREIGN PATENT DOCUMENTS

| | | | |
|---|---|---|---|
| 0164148 | 10/1985 | European Pat. Off. | 128/770 |
| 8504089 | 9/1985 | World Int. Prop. O. | 128/770 |

*Primary Examiner*—Max Hindenburg
*Attorney, Agent, or Firm*—Quarles & Brady

[57] ABSTRACT

A relatively painless method of safely collecting and testing blood comprises piercing a patient's skin, bathing the pierced area with a vehicle liquid and collecting a sample of the vehicle liquid and any blood on a test disk in the apparatus. A novel disposable apparatus for practicing the method also is described.

4 Claims, 1 Drawing Sheet

BLOOD COLLECTION AND TESTING METHOD

RELATED CASE

The present application is a continuation-in-part of copending application U.S. Ser. No. 07/147, 138 filed Jan. 22, 1988, now abandoned.

FIELD OF THE INVENTION

The present application relates to the collection and testing of cutaneous blood and blood components. More particularly, it relates to a method and apparatus for the safe, minimally-invasive, relatively painless, transcutaneous, concurrent collection of a blood sample and the testing for blood components.

DESCRIPTION OF THE PRIOR ART

In the past, researchers and clinicians requiring a sample of the blood for testing of an animal or human have usually obtained that sample by either piercing or nicking the skin of the human or animal and then collecting the sample from a vein, capillary or artery. At times the sample was collected with the assistance of a vacuum. The sample was then processed and a diagnostic test run separately. The method was always painful.

An important aspect of diagnostics has been dangerously underestimated and neglected. For over one hundred years these same, now antiquated blood sampling procedures have been used, with little concern for the spread of blood-borne disease, such as hepatitis B or HTLV of Acquired Immune Deficiency (AIDS). Even today, with the advent of sophisticated "high tech" diagnostics, blood may be grossly smeared over the patient, the phlebotomist and the environment of the sampling area and used contaminated devices are often transported or disposed of by inconvenient methods.

It would be advantageous to have a method and apparatus for the relatively painless collecting, and testing of blood with exceedingly little risk of fluid contact to the nurse or the phlebotomist performing the service, and with much less trauma to the patient.

SUMMARY OF THE PRESENT INVENTION

It is the general object of the present invention to disclose a safe, minimally-invasive, relatively painless method and apparatus for the collection, and testing of blood for specific components.

Briefly stated, the method of the present invention comprises pretreating the external surface of an area of the skin of a human or animal to anesthetize it and to make it antiseptic; piercing the skin in on that area, without significant pain; bathing that area of the skin with a vehicle liquid; collecting a sample comprising the vehicle liquid and blood from the area on a test medium; and testing the sample for one or more diagnostic purposes. The method requires only a very small (about 10 microliters) amount of blood. No excess is collected, wasted or spread. In addition, the procedure is essentially painless and non-invasive. If desired, the method can include inactivating any virus that may be present in the sample.

When the apparatus of the present invention is employed, neither the blood nor contaminated parts are exposed to spread disease. Furthermore the patient is not traumatically exposed to the piercing member, because it is hidden from the patient's view.

The apparatus of the present invention basically comprises a member having a supporting base with an upright piercing pin; a resilient, collapsible cover attached at the bottom to the base and having an open top; a porous test disk, which may contain test reagents which will react with specific substances if they are present; and a reservoir formed by the base and cover which contains a vehicle liquid which is used to transport the blood from the pierced area to the test disk. The preferred apparatus also includes a protective cap and seals and means for dulling nerve endings by pressure dispersal.

Objects and advantages, in addition, to those described will become apparent to those skilled in the art from the description and drawings.

DESCRIPTION OF THE PREFERRED EMBODIMENT

In FIGS. 1 to 4 of the drawings, there is shown an embodiment of an apparatus which can be used in the practice of the method of the present invention.

Figure 1:
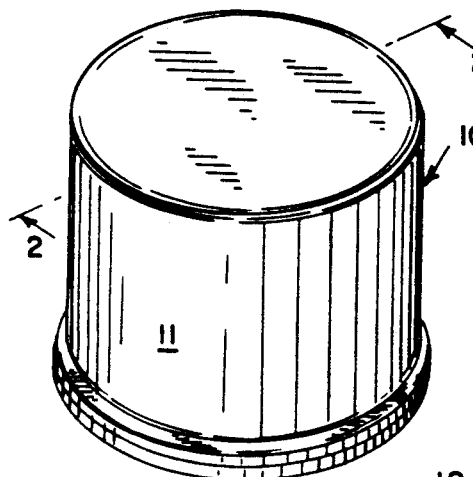
FIG. 1 is a perspective view of a preferred embodiment of the apparatus of the present invention packaged prior to use.
Figure 2:
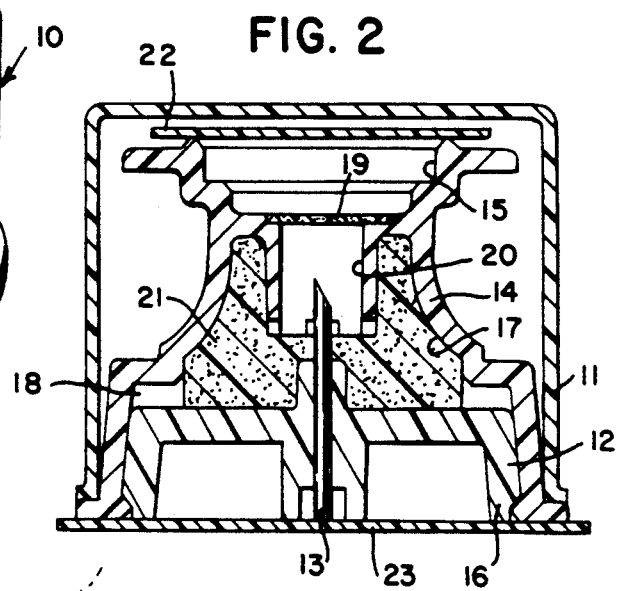
FIG. 2 is a sectional view taken along lines 2—2 of FIG. 1.

Referring to FIGS. 1 and 2, it can be seen that the apparatus 10 is protected prior to use by a cap 11. As seen in FIG. 2, the apparatus 10 includes a supporting base 12 with an upright piercing pin 13. The apparatus 10 also includes a resilient, collapsible cover 14 which has a cup shaped top 15 and which is sealed at its bottom 16 to the base 12. The collapsible resilient, collapsible cover 14 and the base 12 form an internal reservoir 17 for a vehicle liquid 18.

Figure 3:
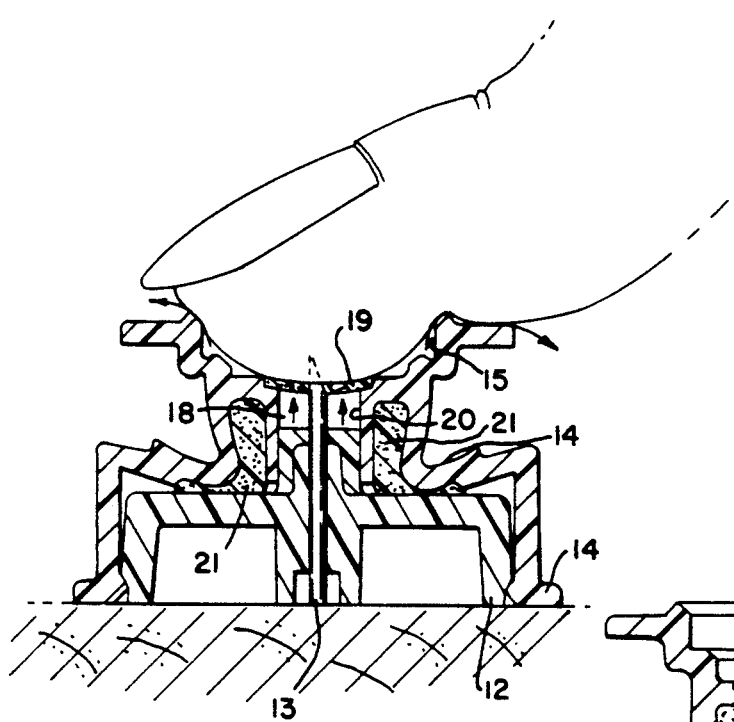
FIG. 3 is a schematic view showing the apparatus being collapsed and used in the practice of the method of the present invention.
Figure 4:
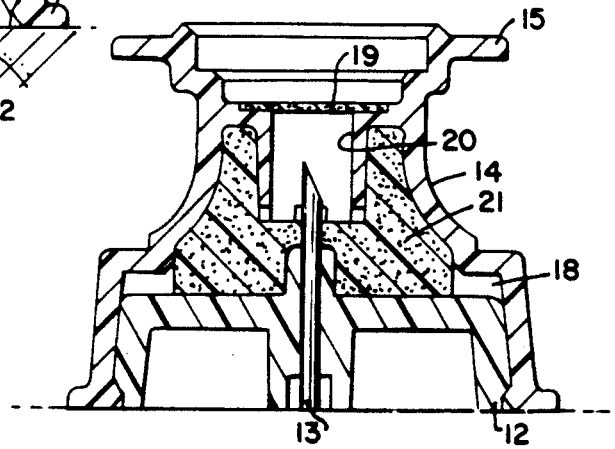
FIG. 4 is a view showing the apparatus after the skin has been pierced, and the apparatus is no longer collapsed.

As seen best in FIGS. 2, 3 and 4, the open top 15 of the cover 14 is closed by a porous test disk 19.

Referring to FIGS. 2 and 4, it can be seen that the piercing pin 13 is positioned directly below the open top 15 of the cover 14 and it extends into the open mouth of a tubular projection 20 which depends downwardly from the cover 14.

The apparatus 10 is normally supplied sterile with a sponge 21 containing a vehicle liquid 18 in the reservoir 17. The apparatus is protected from the contamination by the outer cap 11, the top seal 22 and the bottom seal 23 which are best seen in FIG. 2.

To use the apparatus 10, the cap 11 and top seal 22 are first removed. The apparatus 10 is then placed, as seen in FIG. 3, upon an unyielding surface and the finger of the patient from whom the sample is to be collected is placed in the cup shaped top 15 of the apparatus 10. The skin of the finger, which has been previously sterilized and anesthetized, is then pierced by pressing the finger down on the top of the apparatus 10 until the cover 14 collapses and the piercing pin 13 pierces the skin. The nerve endings in the area to be pierced are further dulled by the pressure dispersal; thus making the piercing relatively painless. The pierced skin area is bathed in vehicle liquid 18 which is forced from the sponge 21 in the reservoir 17 up the tubular projection 20 through the porous test disk 19. At the same time any air in the cupshaped top 15 is forced out. The flow patterns of the vehicle liquid and the air are shown by arrows in FIG. 3. After the skin has been pierced, the finger is kept in contact with the cup shaped top 15 and the downward pressing force is relieved allowing the cover 14 to resume the uncollapsed position seen in FIGS. 2 and 4. As the cover 14 assumes its original position a vacuum or area of reduced pressure is created in the reservoir 17 and mixture of the vehicle liquid and any blood from the pierced area are drawn back onto and through the test disk 19. In the preferred embodiment of the invention, the disk 19 contains reagents which will react with specific substances, if present, in the blood to effect a color change. The results of the tests can be read visually or read by mechanical or electrical means.

Although a specific device for piercing the skin and collecting and testing the blood components has been described, it will be apparent to those skilled in the art that the apparatus of the invention may take other forms.

In the preferred practice of the method of the present invention, the skin is first pretreated with a solution containing anesthetic and antiseptic agent, such as Lidocaine Hydro-chloride and Benzalkonium Chloride, respectively.

The pretreatment solution might be applied by spraying or in a gel-like binder, or with a bandage-like applicator. The solution could contain specific antiviral agents, or general antibacterial-antiviral-antifungal such as nonoxynol-9 (Decon Laboratories, Inc.), formalin or Betapropiolacton,, Binary ethylenediamine, and Psoralen photo chemical inactivation (Hyclone Laboratories, Inc,; *Art to Science,* Vol. 5, No. 3:4–5). The choice of chemical viral inactivator depends on which test will be made on the sample.

The preferred vehicle liquid contains a surface active agent, such as a nonionic detergent, and an anticoagulant agent to fluidize the sample to avoid coagulation and hemolysis, such as sodium heparin and saline. It may also contain solvents such as poly-vinyl acetate, acetone and DMSO (Dimethylsulfoxide) to change the chemical nature of the sample, and analgesic and a gel or cream of high viscosity to help the cup shaped top 15 form a seal with the skin. The vehicle liquid can also contain other anticoagulants or chelating agents and buffering with carrier molecules to avoid nonspecific losses due to binding or deterioration and to promote preservation and inactivate virus. The vehicle liquid also could contain chemicals to inactivate other potential pathogens. Alternately it could enhance or grow pathogens for testing or nonpathogens as a means of detection.

The preferred vehicle liquid contains the following ingredients:

| COMPONENTS OF THE VEHICLE LIQUID | | | |
|---|---|---|---|
| Ingredients | Generic Name Active Component | Preferred Concentration | Concentration Range, Active |
| Heparin | Sodium Heparin | 50 IU/cc | 5–100 IU/cc |
| Saline Buffered Solution | Phosphate Buffered Saline Solution (Sodium Chloride) | .U5M Buffer (pH 7.2) .45M NaCl | pH 4–8 U.2–.9M |
| | NaCl | | |

In addition, EDTA (0.1%) or even vasodilating compounds may be used, such as phenylephrine Hydrochloride. Vasodilators are preferred if more blood cells as compared to immunoglobulins are desired. Vasorestrictors can be used to prevent further bleeding at the nick.

In addition, Triton X-100 or other surface agents providing the same function and not having any detrimental effects on the test but which will inactivate any virus that may be present can also be used. Representative of such surface active agents are the following: Nonidet P-40 (Shell Oil), guanidinium chloride,—mercaptoethanol or other nonionic detergents such as those listed in Stromber, K., "Surface-Active Agents for Isolation of the Core Component of Avian Myeloblastosis Virus". Journal of Virology 1972, pp. 684.697.

The preferred anticoagulant solution contains sodium heparin. However, other anticoagulants which may be used include the following: ethylenediaminetetraacetic acid (EDTA) (0.02%), ammonium heparin, sodium citrate, streptokinase or streptodornase. Carrier molecules can be added to prevent nonspecific absorption of desired components or to heal the pierced area.

Other anesthetic and antiseptic agents than Lidocaine (2.5% w/w), Benzalkonium Chloride (0.13% w/w) may be used. Other agents such as methyl salicylate (15.0%) in methanol (70% v/v), ethanol, paraben, methylparaben, providone iodine, phenol (U.5% antibiotics, dimethyl sulfoxide, acetone, polyvinyl-acetate, polyvinyl alcohol, mineral oil, propylene glycol, or polyethylene glycol can be used. In addition, an antibubble agent may be added such as Pourite (Trademark of Analytical Products, Inc., U.S. Pat. No. 4,089,748).

If desired, a pain-depressing agent such as benzocaine or triethanolamine salicylate or a heat stimulating agent like methylsalicylate also may be included along with volatile solvents such as either. Still further the addition of mild enzyme solutions such as trypsin may be useful, depending on the blood component desired in the eluent (to inactivate degrading enzymes).

The preferred method of piercing the skin, collecting blood components and testing comprises:

A. Applying an anesthetic and antiseptic pretreatment solution with a pad to a portion of the tip of a finger for a few seconds;

B. Removing the protective cap 11 and top seal 22 and placing the base 12 of the apparatus 10 upon a supporting surface as seen in FIG. 2;

C. Pressing the tip of a finger lightly on the cup shaped top 15 of the apparatus to form a seal between the finger and the top 15;

D. Then piercing the skin by pressing firmly upon the top of the apparatus with the finger until the resilient cover 14 collapses and the piercing pin 13 pierces the test disk 19 and the skin of finger and vehicle liquid is forced through the porous test disk 19 into contact with the skin and the blood flowing from the pierced skin;

E. Removing the downward pressure on the finger while keeping the finger in contact with the top 15 until the cover 14 assumes its uncollapsed state whereupon the vehicle liquid 18 and any blood are transferred by suction and adsorption to the test disk 19;

F. Wiping the skin area with alcohol or a suitable antiseptic; and,

G. Reading the results of the test.

The practice of the present invention is further illustrated by the example which follows:

EXAMPLE I

SUBJECT—Male, Age 47. a small area (about 2 cm$^2$) of the skin on the patient's finger is treated with Lidocaine, Benzalkonium Chloride for 10 seconds. The finger is then pressed down lightly upon the cup shaped top 15 of an apparatus 10 containing about 200 microliters of buffered heparin in the sponge 21 in the reservoir 17. The finger is then pressed down to cause the side walls of the cover 14 to collapse and telescope whereupon the pin 13 pierces the skin of the finger and the area of piercing is bathed with vehicle liquid from the sponge 21. The downward pressure exerted on the apparatus is then relieved without lifting the finger whereupon the resilient cover resumes its original state creating a vacuum which sucks the vehicle liquid 18 and any blood through and onto the test disk 19 which contains the test reagents. The test results are then read.

In the preferred embodiments, the test reagents are on the disk 19. Alternatively, the apparatus 10 can be prepared without the test reagents being already on the test disk 19 and the reagents can be added after the collection of the blood sample.

TEST I:

GLUCOSE is detected at about 5 mg/dl by a colorimetric reaction using a specific glucose-oxidase/peroxidase and guaiac chromaphore method.

TEST II:

CHOLESTEROL is determined as about 100 mg/dl by a colorimetric reaction using a specific cholesterol esterasecholesterol oxidase—peroxidase and guaiac chromaphore method. The cholesterol test disks are made by mixing in sequence a binder of methylcellulose in water and propanol (50/50); a buffer of citric acid/sodium citrate dissolved in water, pH 6.5–7.0 with sodium taurocholate; an enzyme mixture of cholesterol esterase, cholesterol oxidase and peroxidase; and a chromogen comprised of gum guaiac in propanol. The mixture is applied to filter paper disks and dried to a moisture content of less than 0.2% for storage stability.

It will be apparent to those skilled in the art that there are many reasons why it may be preferable to use the present invention rather than to pierce the skin with a lance or needle followed by separate processing and testing. The procedure of the present invention is minimally invasive and therefore there is less chance of secondary infection because the apparatus can be supplied presterilized and used in a sanitary manner. Another advantage is that the method is relatively painless. In addition, the vehicle liquid and blood or blood components may be obtained by the donor or another person in a one-hand operation, without technical expertise, and is essentially foolproof. Furthermore, the site of extraction is less precise than that required for phelbotomies. Therefore, a sample can be obtained more easily from infants or others with small and damaged veins or in emergency situations. Finally, the visual detection of test changes can be replaced by electronic detectors, if desired. For example, a hand-held colorimeter can be adapted to visualize the test disc within apparatus and the print out the test results.

The method and apparatus of the present invention are of great potential value for use in diagnostic tests which require dilute plasma/serum for doctors/office, home health care and consumer performed diagnostics. An inexpensive apparatus specifically designed for a given test can be supplied completely assembled, sterile and filled with vehicle liquid by a manufacturer with the test filter in place so that all that is required is to use the device and read the results. The devices can then be disposed of without further treatment to inactivate potential virus contaminants.

In addition, it will be apparent to those skilled in the art that the apparatus of the present invention makes it easier to collect blood from persons who are squeamish. With the apparatus of the present invention the pin, which can also be a needle, is not visible at any time to the person from whom the sample is being collected.

It will be apparent to those skilled in the art that a number of modification and changes can be made without departing from the spirit and scope of the invention. Therefore, the invention is not to be limited except by the claims.

I claim:

1. A nominally invasive, safe method for the relatively painless collection, transportation and testing of blood components from a man or animal comprises pretreating a portion of the skin of the man or animal to make it antiseptic; piercing the skin in that area; bathing the area with a vehicle liquid and moisterizing a solid test medium; collecting and transporting a sample blood and the vehicle liquid from the pierced skin area with vacuum assistance onto the solid test medium which has been moistened; and then determining the test results.

2. The method of claim 1 in which the skin is pretreated with a solution which contains an antiseptic and an anesthetic.

3. The method of claim 1 in which the skin is treated with a solution which contains a vasodilator, or anticoagulant.

4. The method of claim 1 in which the sample is treated with a solution which contains an antiviral agent.

* * * * *